(12) United States Patent
    Carpenter

(10) Patent No.: US 9,295,560 B2
(45) Date of Patent: Mar. 29, 2016

(54) ANATOMIC TOTAL DISC REPLACEMENT

(71) Applicant: Clyde T. Carpenter, Olympia, WA (US)

(72) Inventor: Clyde T. Carpenter, Olympia, WA (US)

(*) Notice: Subject to any disclaimer, the term of this patent is extended or adjusted under 35 U.S.C. 154(b) by 380 days.

(21) Appl. No.: 13/741,631

(22) Filed: Jan. 15, 2013

(65) Prior Publication Data

US 2013/0131806 A1    May 23, 2013

Related U.S. Application Data

(63) Continuation of application No. 12/927,079, filed on Nov. 4, 2010, now Pat. No. 8,353,964.

(51) Int. Cl.
    *A61F 2/44*    (2006.01)
    *A61F 2/46*    (2006.01)
    (Continued)

(52) U.S. Cl.
    CPC .............. *A61F 2/442* (2013.01); *A61F 2/441* (2013.01); *A61F 2/4611* (2013.01); *A61F 2/3094* (2013.01); *A61F 2002/2817* (2013.01); *A61F 2002/2835* (2013.01); *A61F 2002/30013* (2013.01); *A61F 2002/30019* (2013.01); *A61F 2002/30075* (2013.01); *A61F 2002/3083* (2013.01); *A61F 2002/30092* (2013.01); *A61F 2002/30133* (2013.01); *A61F 2002/30433* (2013.01); *A61F 2002/30462* (2013.01); *A61F 2002/30467* (2013.01); *A61F 2002/30484* (2013.01); *A61F 2002/30563* (2013.01); *A61F 2002/30578* (2013.01); *A61F 2002/30579* (2013.01); *A61F 2002/30581* (2013.01); *A61F 2002/30604* (2013.01); *A61F 2002/30611* (2013.01); *A61F 2002/30616* (2013.01);
    (Continued)

(58) Field of Classification Search
    CPC .......... A61F 2/44; A61F 2/441; A61F 2/442; A61F 2002/4495
    USPC ............................ 623/17.11–17.16
    See application file for complete search history.

(56) References Cited

U.S. PATENT DOCUMENTS 3,867,728 A    2/1975    Stubstad
4,309,777 A    1/1982    Patil
               (Continued)

FOREIGN PATENT DOCUMENTS

WO    2006073402 A1    7/2006
WO    2009064787 A2    5/2009
WO    2012/061627 A1   5/2012

OTHER PUBLICATIONS

PCM Artificial Cervical Disc, Jan. 10, 2008 [retrieved online May 22, 2009 http://www.neurocirugia.com] 2 pages.

(Continued)

*Primary Examiner* — Mary Hoffman
(74) *Attorney, Agent, or Firm* — Chernoff, Vilhauer, McClung & Stenzel, LLP

(57) ABSTRACT

An artificial spinal disc prosthesis that can be implanted to replace a damaged natural spinal disc. A nucleus of compressible elastomeric material is surrounded by a winding of a slender strand of flexible tension-bearing material oriented at a pitch angle relative to a central axis. The orientation of the winding provides the prosthesis a limited amount of freedom of movement and flexibility. A pair of end caps of the prosthetic implant include angulated grooves that allow for insertion of the device between vertebral bodies from any of several directions. Special fasteners provide protruding points useful in anchoring the prosthesis.

19 Claims, 6 Drawing Sheets

(51) Int. Cl.
*A61F 2/30* (2006.01)
*A61F 2/28* (2006.01)

(52) U.S. Cl.
CPC ............... *A61F 2002/30774* (2013.01); *A61F 2002/30784* (2013.01); *A61F 2002/30787* (2013.01); *A61F 2002/30831* (2013.01); *A61F 2002/30841* (2013.01); *A61F 2002/30952* (2013.01); *A61F 2002/4495* (2013.01); *A61F 2002/4625* (2013.01); *A61F 2310/00017* (2013.01); *A61F 2310/00023* (2013.01); *A61F 2310/00029* (2013.01); *A61F 2310/00047* (2013.01); *A61F 2310/00053* (2013.01); *A61F 2310/00131* (2013.01); *A61F 2310/00604* (2013.01); *A61F 2310/00796* (2013.01); *A61F 2310/00976* (2013.01)

(56) References Cited

U.S. PATENT DOCUMENTS

| | | |
|---|---|---|
| 4,349,921 A | 9/1982 | Kuntz |
| 4,759,766 A | 7/1988 | Buettner-Janz |
| 4,759,769 A | 7/1988 | Hedman |
| 4,863,477 A | 9/1989 | Monson |
| 4,911,718 A | 3/1990 | Lee |
| 4,917,704 A | 4/1990 | Frey |
| 4,932,969 A | 6/1990 | Frey |
| 4,946,378 A | 8/1990 | Hirayama |
| 4,955,908 A | 9/1990 | Frey |
| 5,002,576 A | 3/1991 | Fuhrmann |
| 5,071,437 A | 12/1991 | Steffee |
| 5,108,438 A | 4/1992 | Stone |
| 5,108,442 A | 4/1992 | Smith |
| 5,123,926 A | 6/1992 | Pisharodi |
| 5,171,281 A | 12/1992 | Parsons |
| 5,246,458 A | 9/1993 | Graham |
| 5,258,031 A | 11/1993 | Salib |
| 5,306,307 A | 4/1994 | Senter |
| 5,306,309 A | 4/1994 | Wagner |
| 5,314,477 A | 5/1994 | Marnay |
| 5,320,644 A | 6/1994 | Baumgartner |
| 5,370,697 A | 12/1994 | Baumgartner |
| 5,401,269 A | 3/1995 | Buttner-Janz |
| 5,425,773 A | 6/1995 | Boyd |
| 5,456,722 A | 10/1995 | McLeod |
| 5,458,642 A | 10/1995 | Beer |
| 5,514,180 A | 5/1996 | Heggeness |
| 5,522,899 A | 6/1996 | Michelson |
| 5,534,029 A | 7/1996 | Shima |
| 5,534,030 A | 7/1996 | Navarro |
| 5,534,031 A | 7/1996 | Matsuzaki |
| 5,545,229 A | 8/1996 | Parsons |
| 5,556,431 A | 9/1996 | Buttner-Janz |
| 5,562,738 A | 10/1996 | Boyd |
| 5,645,596 A | 7/1997 | Kim |
| 5,674,294 A | 10/1997 | Bainville |
| 5,674,296 A | 10/1997 | Bryan |
| 5,676,701 A | 10/1997 | Yuan |
| 5,676,702 A | 10/1997 | Ratron |
| 5,683,465 A | 11/1997 | Shinn |
| 5,702,450 A | 12/1997 | Bisserie |
| 5,755,797 A | 5/1998 | Baumgartner |
| 5,776,196 A | 7/1998 | Matsuzaki |
| 5,800,547 A | 9/1998 | Schafer |
| 5,824,094 A | 10/1998 | Serhan |
| 5,827,328 A | 10/1998 | Buttermann |
| 5,861,041 A | 1/1999 | Tienboon |
| 5,865,846 A | 2/1999 | Bryan |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima |
| 5,961,554 A | 10/1999 | Janson |
| 5,976,181 A | 11/1999 | Whelan |
| 5,981,826 A | 11/1999 | Ku |
| 5,989,291 A | 11/1999 | Ralph |
| 6,001,130 A | 12/1999 | Bryan |
| 6,015,436 A | 1/2000 | Schonhoffer |
| 6,019,792 A | 2/2000 | Cauthen |
| 6,019,793 A | 2/2000 | Perren |
| 6,022,376 A | 2/2000 | Assell |
| 6,039,763 A | 3/2000 | Shelokov |
| 6,093,205 A | 7/2000 | McLeod |
| 6,110,210 A | 8/2000 | Norton |
| 6,113,637 A | 9/2000 | Gill |
| 6,132,465 A | 10/2000 | Ray |
| 6,136,031 A | 10/2000 | Middleton |
| 6,146,421 A | 11/2000 | Gordon |
| 6,146,422 A | 11/2000 | Lawson |
| 6,156,067 A | 12/2000 | Bryan |
| 6,162,252 A | 12/2000 | Kuras |
| 6,165,218 A | 12/2000 | Husson |
| 6,176,882 B1 | 1/2001 | Biedermann |
| 6,179,874 B1 | 1/2001 | Cauthen |
| 6,187,043 B1 | 2/2001 | Ledergerber |
| 6,187,048 B1 | 2/2001 | Milner |
| 6,228,118 B1 | 5/2001 | Gordon |
| 6,231,605 B1 | 5/2001 | Ku |
| 6,240,926 B1 | 6/2001 | Chin Gan |
| 6,283,998 B1 | 9/2001 | Eaton |
| 6,296,664 B1 | 10/2001 | Middleton |
| 6,315,797 B1 | 11/2001 | Middleton |
| 6,325,827 B1 | 12/2001 | Lin |
| 6,348,071 B1 | 2/2002 | Steffee |
| 6,368,350 B1 | 4/2002 | Erickson |
| 6,375,682 B1 | 4/2002 | Fleischmann |
| 6,395,032 B1 | 5/2002 | Gauchet |
| 6,402,785 B1 | 6/2002 | Zdeblick |
| 6,419,704 B1 | 7/2002 | Ferree |
| 6,419,706 B1 | 7/2002 | Graf |
| 6,425,919 B1 | 7/2002 | Lambrecht |
| 6,436,143 B1 | 8/2002 | Ross |
| 6,440,168 B1 | 8/2002 | Cauthen |
| 6,454,806 B1 | 9/2002 | Cohen |
| 6,458,159 B1 | 10/2002 | Thalgott |
| 6,482,234 B1 | 11/2002 | Weber |
| 6,520,996 B1 | 2/2003 | Manasas |
| 6,533,817 B1 | 3/2003 | Norton et al. |
| 6,540,785 B1 | 4/2003 | Gill |
| 6,579,318 B2 | 6/2003 | Varga |
| 6,579,320 B1 | 6/2003 | Gauchet |
| 6,582,468 B1 | 6/2003 | Gauchet |
| 6,592,624 B1 | 7/2003 | Fraser |
| 6,602,291 B1 | 8/2003 | Ray |
| 6,610,094 B2 | 8/2003 | Husson |
| 6,620,196 B1 | 9/2003 | Trieu |
| 6,626,943 B2 | 9/2003 | Eberlein et al. |
| 6,645,248 B2 | 11/2003 | Casutt |
| 6,679,915 B1 | 1/2004 | Cauthen |
| 6,682,562 B2 | 1/2004 | Viart |
| 6,706,068 B2 | 3/2004 | Ferree |
| 6,712,853 B2 | 3/2004 | Kuslich |
| 6,719,796 B2 | 4/2004 | Cohen |
| 6,723,097 B2 | 4/2004 | Fraser |
| 6,726,720 B2 | 4/2004 | Ross |
| 6,733,533 B1 | 5/2004 | Lozier |
| 6,736,850 B2 | 5/2004 | Davis |
| 6,746,485 B1 | 6/2004 | Zucherman |
| 6,749,635 B1 | 6/2004 | Bryan |
| 6,770,094 B2 | 8/2004 | Fehling |
| 6,786,930 B2 | 9/2004 | Biscup |
| 6,958,077 B2 | 10/2005 | Suddaby |
| 6,966,931 B2 | 11/2005 | Huang |
| 6,981,989 B1 | 1/2006 | Fleischmann |
| 6,994,727 B2 | 2/2006 | Khandkar |
| 7,060,097 B2 | 6/2006 | Fraser |
| 7,060,100 B2 | 6/2006 | Ferree |
| 7,066,960 B1 | 6/2006 | Dickman |
| 7,083,651 B2 | 8/2006 | Diaz |
| 7,153,325 B2 | 12/2006 | Kim |
| 7,156,848 B2 | 1/2007 | Ferree |
| 7,192,447 B2 | 3/2007 | Rhoda |
| 7,195,644 B2 | 3/2007 | Diaz |

(56) References Cited

U.S. PATENT DOCUMENTS

| | | |
|---|---|---|
| 7,214,243 B2 | 5/2007 | Taylor |
| 7,235,103 B2 | 6/2007 | Rivin |
| 7,250,060 B2 | 7/2007 | Trieu |
| 7,291,171 B2 | 11/2007 | Ferree |
| 7,291,172 B2 | 11/2007 | Marissen |
| 7,320,707 B2 | 1/2008 | Zuckerman |
| 7,364,589 B2 | 4/2008 | Eisermann |
| 7,419,505 B2 | 9/2008 | Fleischmann |
| 7,452,379 B2 | 11/2008 | Mitchell |
| 7,458,988 B2 | 12/2008 | Trieu |
| 7,534,268 B2 | 5/2009 | Hudgins |
| 7,682,540 B2 | 3/2010 | Boyan |
| 7,731,753 B2 | 6/2010 | Reo et al. |
| 7,887,592 B2 | 2/2011 | Koske |
| 2003/0045939 A1 | 3/2003 | Casutt |
| 2004/0083000 A1 | 4/2004 | Keller |
| 2004/0093087 A1 | 5/2004 | Ferree |
| 2004/0215342 A1 | 10/2004 | Suddaby |
| 2005/0021146 A1 | 1/2005 | de Villiers |
| 2005/0043796 A1 | 2/2005 | Grant et al. |
| 2005/0055099 A1 | 3/2005 | Ku |
| 2005/0197702 A1 | 9/2005 | Coppes |
| 2005/0197706 A1 | 9/2005 | Hovorka |
| 2005/0228500 A1 | 10/2005 | Kim |
| 2005/0251260 A1 | 11/2005 | Gerber |
| 2005/0283237 A1 | 12/2005 | Zuchermann |
| 2006/0149371 A1 | 7/2006 | Marik |
| 2006/0241767 A1 | 10/2006 | Doty |
| 2006/0276900 A1 | 12/2006 | Carpenter |
| 2007/0032873 A1 | 2/2007 | Pisharodi |
| 2007/0050032 A1 | 3/2007 | Gittings |
| 2007/0055265 A1 | 3/2007 | Schaller |
| 2007/0073311 A1 | 3/2007 | Williams |
| 2007/0088441 A1 | 4/2007 | Duggal |
| 2007/0100453 A1 | 5/2007 | Parsons |
| 2007/0100454 A1 | 5/2007 | Burgess |
| 2007/0118221 A1 | 5/2007 | Robie et al. |
| 2007/0162133 A1 | 7/2007 | Doubler |
| 2007/0239277 A1 | 10/2007 | Berger et al. |
| 2007/0265626 A1 | 11/2007 | Seme |
| 2007/0270952 A1 | 11/2007 | Wistrom |
| 2008/0033563 A1 | 2/2008 | Khandkar |
| 2008/0077242 A1 | 3/2008 | Reo |
| 2008/0077244 A1 | 3/2008 | Robinson |
| 2008/0103599 A1 | 5/2008 | Kim |
| 2008/0215156 A1 | 9/2008 | Duggal |
| 2008/0221689 A1 | 9/2008 | Chaput |
| 2008/0288077 A1 | 11/2008 | Reo et al. |
| 2009/0062920 A1 | 3/2009 | Tauber |
| 2009/0069895 A1 | 3/2009 | Gittings |
| 2009/0069896 A1 | 3/2009 | Reo |
| 2009/0076612 A1 | 3/2009 | Reo |
| 2009/0118835 A1 | 5/2009 | Robinson |
| 2009/0138084 A1 | 5/2009 | Conner |
| 2010/0286783 A1 | 11/2010 | Lechmann et al. |

OTHER PUBLICATIONS

Bryan Cervical Disc—Los Angeles Spine Surgeons [retrieved online May 22, 2009 http://www.spineexperts.com] 1 page.

Lumbar Spinal Fusion Myths and Disk Replacement Realities, John H. Peloza, M.D. [retrieved online May 22, 2009 http://www.centerforspinecare.com] 7 pages.

Total Disk Replacement, Jack Zigler, MD [retrieved online Sep. 29, 2010 http://www.spine-health.com] 4 pages.

International Search Report and Written Opinion, PCT/US11/59203, dated Mar. 1, 2012 7 pages.

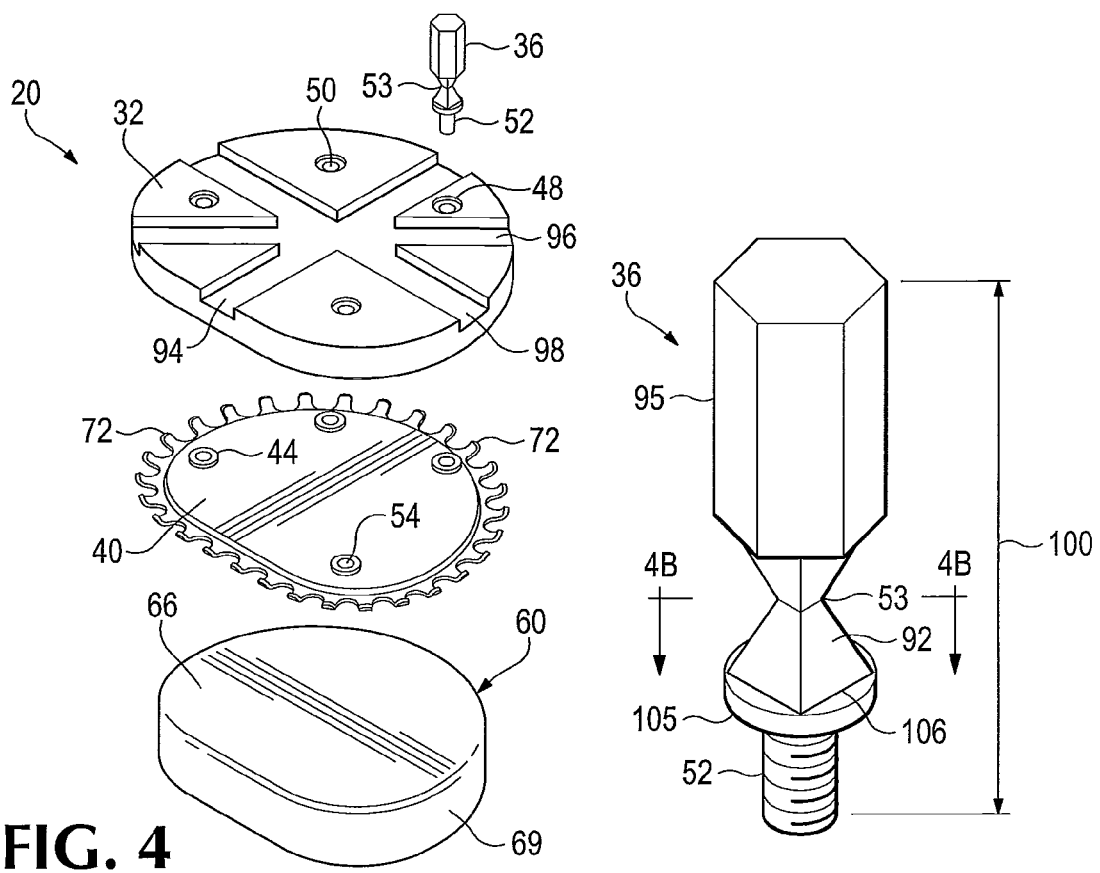
FIG. 4
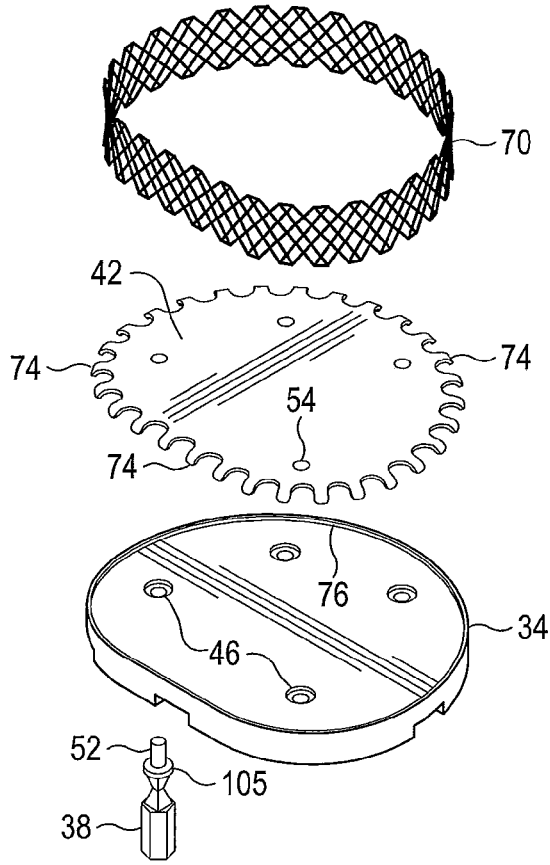
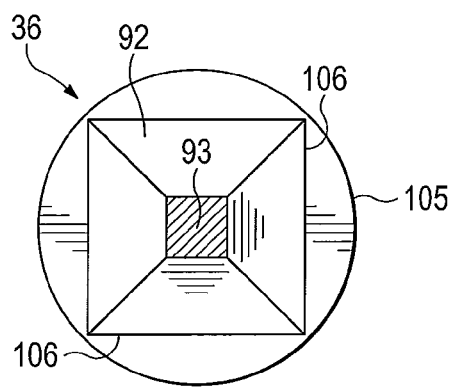
FIG. 4A
FIG. 4B

ANATOMIC TOTAL DISC REPLACEMENT

FIELD OF THE INVENTION

The present invention relates to a prosthetic intervertebral disc which provides for continued mobility and which is intended to replace a diseased intervertebral disc.

BACKGROUND OF THE INVENTION

The vertebrate spine is made of bony structures called vertebral bodies that are separated by soft tissue structures called intervertebral discs. The intervertebral disc is commonly referred to as a spinal disc. The spinal disc serves as a mechanical cushion and a connection between the vertebral bodies, permitting controlled motions between vertebral segments of the axial skeleton. The disc acts as a synchondral joint and allows physiologic degrees of flexion, extension, lateral bending, and axial rotation of adjacent vertebral bodies relative to one another. The disc must allow these motions and yet must have sufficient elastic strength to resist the external forces and torsional moments caused by the vertebral bodies.

The normal disc is a mixed avascular structure comprising two vertebral end plates ("end plates"), an annulus fibrosis ("annulus") and a nucleus pulposus ("nucleus"). The end plates are composed of thin cartilage overlying a thin layer of hard, cortical bone. The end plates act to attach the disc to the spongy cancellous bone of the vertebral bodies.

The annulus of the disc is a tough, outer fibrous ring about 10 to 15 millimeters in height and about 15 to 20 millimeters in radial thickness. The structure of the annulus is somewhat like an automobile tire, with 15 to 20 overlapping plies. Its fibers extend generally helically and are inserted into the superior and inferior vertebral bodies at a roughly 30-40 degree angle to the central axis of the spine in both directions. This configuration particularly resists torsion, as about half of the angulated fibers will tighten when the vertebrae rotate in either direction, relative to each other. The laminated plies of the annulus are less firmly attached to each other. The attached fibers also prevent the disc from extruding laterally as a consequence of the complex twisting motion of the spine.

Inside the annulus is a gel-like nucleus with high water content. The nucleus acts as a liquid to equalize pressures within the annulus. The material consistency and shape of a normal nucleus pulposis is similar to the inside of a jelly doughnut. The loose fluid-like nature allows the nucleus to shrink with compressive forces or swell from osmotic pressure. The ion concentration of the nucleus can create an osmotic swelling pressure of about 0.1 to about 0.3 MPa. As a result, the gel-like nucleus can support an applied load yet can be compressed or temporarily deformed to a limited extent. Together, the annulus and nucleus support the spine while flexing, extending, compressing, or rotating in response to forces produced by the adjacent vertebral bodies during bending, lifting, etc.

The compressive load on the disc changes with posture. For example, when the human body is supine, the compressive load on the third lumbar disc is about 300 Newtons (N), which rises to about 700 N when an upright stance is assumed. The compressive load increases yet again, to 1200 N, when the body is bent forward by only 20 degrees. Resultant pressure within the nucleus pulposis of a spinal disc similarly varies between, for example, 0.5 MPa when in a relaxed standing posture, to 2.3 MPa or more when lifting a weight with the back roundly flexed.

A spinal disc may be displaced or damaged due to trauma or a disease process. A disc herniation occurs when the annulus fibers are weakened or torn and the inner material of the nucleus becomes permanently bulged, distended, or extruded out of its normal, internal annular confines The mass and/or physiologic reaction of a herniated or "slipped" nucleus tissue can compress a spinal nerve, resulting in leg pain, loss of muscle strength and control, and even paralysis. Alternatively, with discal degeneration, the nucleus loses its water binding ability and dehydrates with consequent loss in disc height. Consequently, the volume of the nucleus decreases, causing the annulus to buckle in areas where the laminated plies are loosely bonded. As these overlapping plies of the annulus buckle and separate, either circumferential or radial tears may occur in the annulus, potentially resulting in persistent and disabling back pain. Adjacent, ancillary facet joints between vertebrae bones may also be forced into an overriding position, which may cause additional back pain. The most frequent site of occurrence of a herniated disc is in the lower lumbar region. The cervical spinal discs are also commonly affected.

In the United States, low back pain accounts for the loss of many workdays. Degeneration of an intervertebral disc is one of the most common causes of low back pain and therefore frequently requires treatment. When conservative treatment such as activity modification, medications, physical therapy, or chiropractic manipulation fail, more aggressive measures, such as surgical treatment, may be required. Spinal fusion has been the mainstay of surgical treatment for recalcitrant low back pain secondary to a degenerated disc, but spinal fusion causes stiffness of the vertebral segment and therefore places increased stresses on adjacent vertebral levels. Replacement of the intervertebral disc with a device that maintains the height of the disc while still maintaining compressibility and motion is highly desirable and is likely to decrease the back pain associated with a diseased intervertebral disc.

An early design for an artificial disc was primarily a round stainless steel ball intended to replace the intervertebral disc. This resulted in the steel ball subsiding into the vertebral body and did not maintain disc height nor provide compressibility. Subsequent designs of intervertebral disc replacements incorporated a ball and socket design but used metal end plates to fit adjacent to the vertebral bodies to prevent subsidence. Most disc replacements of this ball and socket type of design do not allow for a mobile center of rotation in both the axial plane and the sagittal plane. Many of these designs also lack any type of resiliently compressible material within the device to absorb compressive forces.

Other designs for artificial disc replacement incorporate some form of compressive springs. This may result in motion of metal on metal where the springs are attached to the endplates. This potentially causes release of metal particulate debris into the tissues, which can stimulate foreign body reaction. Foreign body reactions can result in resorption of adjacent bone and subsequent subsidence, loosening and pain. Other problems with compressive spring-type prostheses are that they do not resist translational forces well and will eventually fatigue. These devices also lack a mobile instantaneous axis of rotation.

Some current disc prostheses include a solid core of an elastomeric material, such as a polyolefin, to act as a compressible core between two metal end plates. Devices of this type present the problem of having to attach a substance of consistent elasticity to a metal end plate. These devices do not resist shear or translational forces well.

What is desired, then, is a prosthetic spinal disc able to allow limited flexion and rotation of vertebra bodies between which the prosthesis is implanted, which is compressible, and which can be implanted using a selected one of several different approach directions.

SUMMARY OF THE INVENTION

The invention disclosed herein and defined by the claims that are a part of this disclosure provides answers to some of the aforementioned shortcomings and disadvantages of the previously developed spinal disc prostheses. Disclosed herein is a novel disc prosthesis that is anatomically configured to fit into the intervertebral disc space after complete removal of a diseased intervertebral disc. The spinal disc replacement disclosed herein is flexible yet strong and can act as a mechanical shock absorber and allow spinal flexibility and motion between the vertebrae.

In one embodiment the prosthesis disclosed can be used as a permanent implant to replace a spinal disc.

In one embodiment, the spinal disc prosthesis may have a winding of slender flexible tension-bearing members on finger-like hooks spaced apart about the peripheries of a pair of end plates so that the tension-bearing members are in a helical orientation. These tension-bearing members convert compressive forces into tensile forces in a manner similar to action of the annulus of a normal intervertebral disc.

In some embodiments, the end plates (one superior and one inferior) may be of a biocompatible metal such as a titanium alloy or cobalt/chrome alloy.

In one embodiment of the spinal disc prosthesis the winding of tension-bearing members emulates the natural arrangement of fibrous tissue in the normal annulus fibrosis.

In certain embodiments of the spinal disc prosthesis, the windings of tension-bearing members may surround a nucleus that is compressible.

In certain embodiments of the spinal disc prosthesis a nucleus may comprise silicone encapsulated within a container fashioned of a soft biocompatible material.

In some embodiments the tension-bearing members may be wound about finger-like hooks extending radially from the end plates, with end caps fastened to the end plates and capturing the tension-bearing members, keeping them from being disengaged from the hooks.

In various embodiments the orientations of superior and inferior faces of the end caps relative to each other may range from parallel to an angularity appropriate to accommodate the normal lordotic shape of the spine.

In some embodiments, the superior and inferior end caps may have convex outer surfaces to accommodate the concavity present in some human vertebral end plates.

In yet further embodiments the outer surfaces of the end caps may be configured to allow for bone ingrowth into the superior aspect of the superior end plate and into the inferior aspect of the inferior end plate so that the prosthesis attaches itself biologically to the bone of the adjacent vertebral bodies.

In some embodiments, the end caps may each carry an array of small protruding spikes extending from fasteners connecting end caps to the end plates and which serve to engage the adjacent vertebral bodies when the spinal disc prosthesis is implanted.

In one embodiment such a protruding spike may be formed by breaking off a head portion of a special fastener upon installation of the fastener to secure an end cap to an end plate.

The foregoing and other features of the invention will be more readily understood upon consideration of the following detailed description of the invention, taken in conjunction with the accompanying drawings.

BRIEF DESCRIPTION OF THE DRAWINGS

FIG. 4 is an exploded isometric view of the disc prosthesis shown in FIG. 2.

FIG. 4A is an isometric view, at an enlarged scale, of one of the screws used to interconnect an end plate with an end cap.

FIG. 4B is a section view taken along line 4B-4B of FIG. 4A.

DETAILED DESCRIPTION OF EMBODIMENTS

As used herein, references to certain directions and orientations such as, for example, superior (towards the head), inferior (towards the feet), lateral (towards the side), medial (towards the midline), posterior (towards the back), and anterior (towards the front refer to such directions and orientations in a standing human. As they are applied to embodiments of the invention, it will be further understood that such directions and orientations refer to the position of such embodiments within a human after implantation, when the human is standing upright.

Unless specified otherwise, a physical property designated herein for a particular embodiment will be considered to be met provided its value is within 10% of the specified value of the physical property. For example, if a value for a distance in an embodiment of the invention is specified to be 10 cm, then it will be understood that embodiments of 9 to 11 cm are within the scope of the disclosure.

Figure 1:
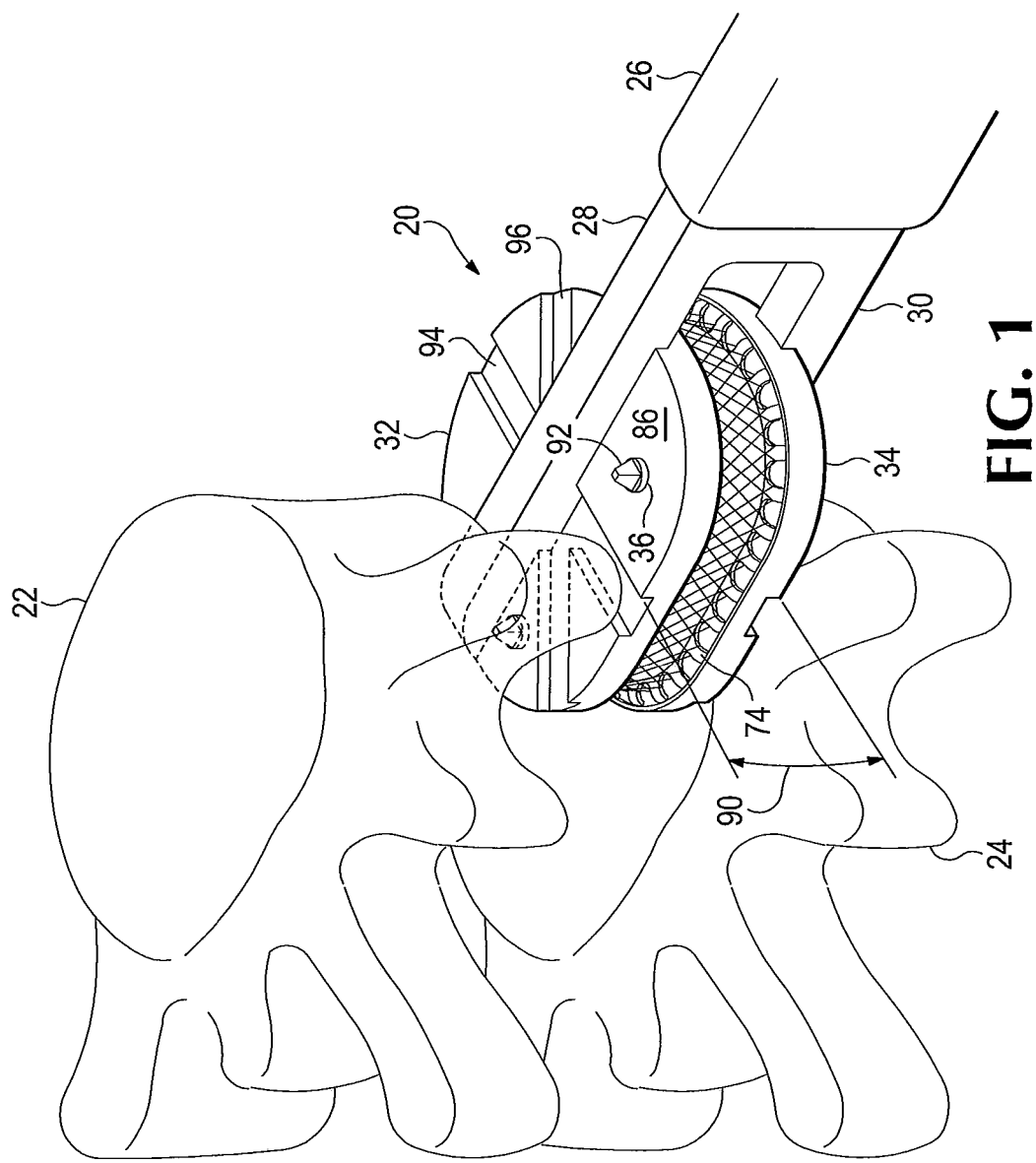
FIG. 1 is an isometric view showing a prosthetic intervertebral disc held in a tool and being inserted between a pair of vertebral bodies.

As shown in FIG. 1, a prosthetic intervertebral disc 20 as disclosed herein is intended to fit into the intervertebral space between a pair of vertebral bodies 22 and 24 to replace a diseased natural intervertebral disc which has been completely removed surgically. The vertebral body 22 may be an L-4 vertebra and the vertebral body 24 may be an L-5 vertebra, for example. As shown, the prosthetic intervertebral disc 20 (also referred to as a disc prosthesis) is held by an insertion tool 26 shown in a simplified form as having an upper arm 28 and a lower arm 30 engaging an upper end cap 32 and a lower end cap 34 of the prosthetic intervertebral disc 20, as will be explained in greater detail below.

Figure 2:
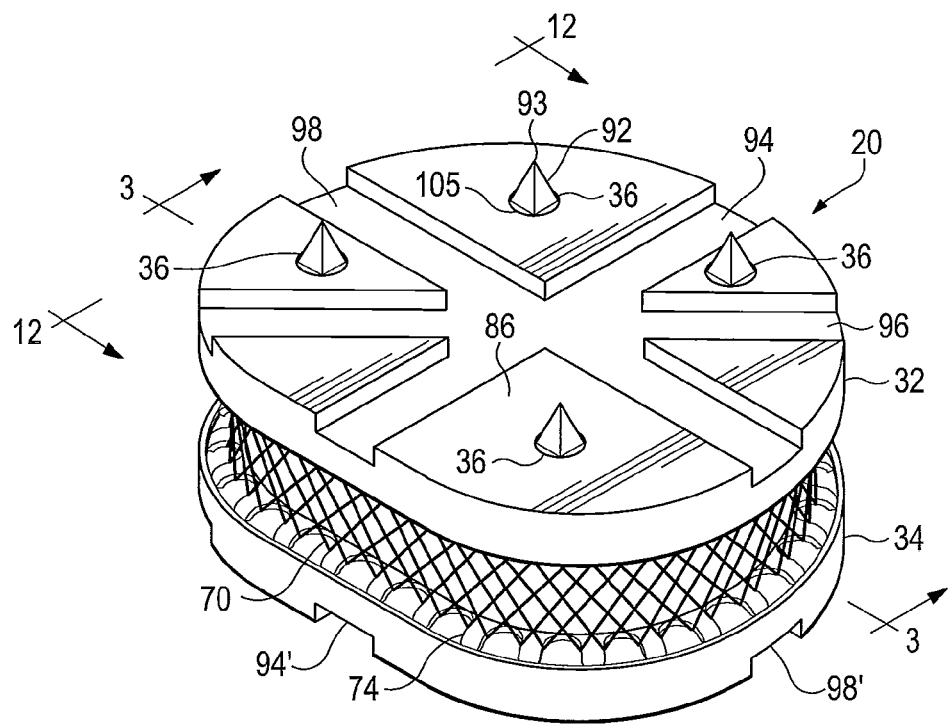
FIG. 2 is an isometric view of the spinal disc prosthesis shown in FIG. 1.
Figure 3:
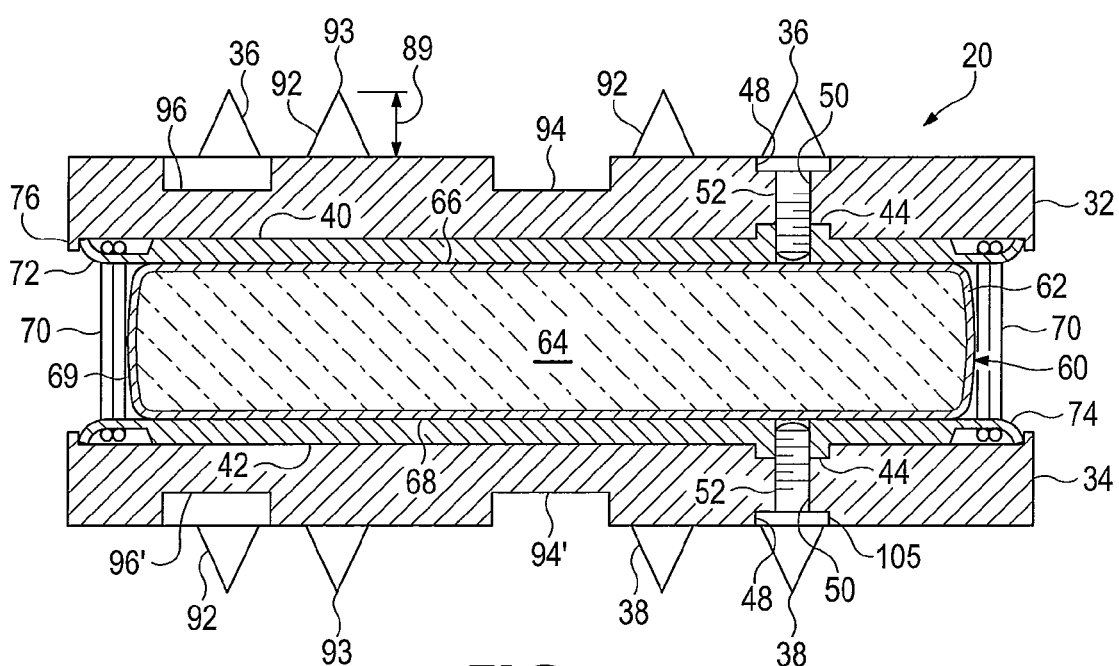
FIG. 3 is a sectional view of the disc prosthesis, taken along line 3-3 of FIG. 2, at an enlarged scale.

Referring next FIGS. 2 and 3, the end caps 32 and 34 are attached to the prosthetic intervertebral disc 20 by fasteners 36 and 38 that extend through the end caps 32 and 34 into an upper end plate 40 and a lower end plate 42. Bosses 44 may be provided on the end plates 40 and 42 for each of the fasteners 36 and 38, and a corresponding cavity 46 may be provided in each end cap 32 and 34 to receive each boss 44 and thereby establish the proper location of the end cap 32 or 34 with respect to the end plate 40 or 42.

Respective recesses 48 may be provided in an exterior face of each of the end caps 32 and 34 to receive the fasteners 36 and 38, and a bore 50 may be located centrally within each recess 48 to accept the threaded shaft 52 of a respective fastener 36 or 38. Threaded bores 54 are located within the bosses 44 to engage with the threaded shafts 52 of the fasteners 36 and 38, so that the fasteners 36 and 38, when tightened, can securely fasten the end caps 32 and 34 to the end plates 40 and 42.

Between the end plates 40 and 42 is a nucleus 60. The nucleus 60 may be an elastomeric body of a compressible material contained in a flexible reinforced bag 62 that is and has the required elastomeric properties to support the compressive loads that are normally imposed upon a natural intervertebral disc, as will be explained more fully below. The end plates 40 and 42 are held together, adjacent respectively an upper face 66 and a lower face 68 of the nucleus 60, by a part serving as the prosthetic equivalent of the natural annulus, in the form of a winding 70 of tension-carrying material interconnecting the upper and lower end plates 40 and 42.

In one form of the nucleus 60, an appropriately shaped flexible container in the form of a suitably shaped and molded flexible outer membrane or cover 62, which may be a bag of thin silicone rubber reinforced by fabric woven of a suitably biocompatible polymer fiber such as ultra high molecular weight polyethylene, may surround and contain a somewhat compressible and flexible elastomeric material such as a gel body 64, or a suitable quantity of water. The gel body 64 may be, for example, of a hydrogel composition such as a silicone.

The nucleus 60 has an upper face 66 adjacent the upper end plate 40, a lower face 68 adjacent the lower end plate 42, and a peripheral, approximately cylindrical peripheral outer surface 69 interconnecting the upper face 66 and the lower face 68.

It is desired to provide sufficient torsional flexibility in the prosthetic intervertebral disc 20 to allow rotation through an angle of at least 2 degrees between the upper and lower end caps 32, 34 of the prosthetic disc with torsions greater than 0.01 N-m, without failing. In preferred embodiments, the prosthetic intervertebral disc 20 can withstand compressive loads of at least 100 MPa without failing. This is much more compliant than previously designed artificial discs, which used metals or high molecular weight polyethylene plastics with a compressive modulus typically greater than 100 MPa. The elasticity of the prosthetic disc 20 disclosed herein thus allows for shock absorption and flexibility.

In general, any biocompatible polymer that can be used for biomedical purposes can be used as a nucleus 60 as long as the polymer exhibits a compressive strength of at least 1 MPa, preferably 10 MPa, when subjected to the loads of the human spine. The polymer should preferably have an ultimate stretch of 15% or greater, and an ultimate tensile or compressive strength of 100 kilopascals or greater. Hydrophilic polymers are preferred for biocompatibility and controlled swelling characteristics. Methods for identifying polymers and other materials of suitable biocompatibility for use in the prosthetic disc disclosed herein are well known in the art (e.g. Taksali S, Grauer J N, and Vaccaro A R., Material considerations for intervertebral disc replacement implants. Spine J November-December 2004; 4(6 Suppl): 231S-238S; Wang Y X, Robertson J L, Spillman W B Jr, and Claus R O. Effects of the chemical structure and the surface properties of polymeric biomaterials on their biocompatibility. Pharm Res. August 2004; 21(8): 1362-73; and Rizzi G, Scrivani A, Fini M, and Giardino R., Biomedical coatings to improve the tissue-biomaterial interface. Int. J. Artif. Organs. August 2004; 27(8): 649-57. Biocompatibility may also be defined by cytotoxicity and sensitivity testing specified by ISO (ISO 10993-5 1999: Biological evaluation of medical devices—Part 5: Tests for in vitro cytotoxicity; and ISO 10993-10 2002: Biological Evaluation of medical devices-Part 10: Tests for irritation and delayed-type hypersensitivity).

Other polymers useful in the nucleus of the disclosed prosthetic disc 20 include silicone rubber, polyvinyl alcohol hydrogels, polyvinyl pyrrolidone, polyurethane/silicon composites, and other materials as disclosed in Stubstad, U.S. Pat. No. 3,867,728, and poly HEMA, HYPAN™ and Salubria™ biomaterial, or other polymers as disclosed in Lee et al., U.S. Pat. No. 4,911,718. In other embodiments the nucleus 60 may be made of or include an elastomeric cryogel material disclosed in U.S. Pat. Nos. 5,981,826 and 6,231,605, hereby incorporated by reference, that has a mechanical compressive modulus of elasticity of about 1.0 MPa, ultimate stretch of greater than 15%, and ultimate strength of about 5 MPa. In some embodiments, cryogels may be prepared from commercially available PVA powders by any of the methods known to the art.

In still other embodiments, suitable polymers for use in the nucleus to achieve the desired range of elastomeric mechanical properties include polyurethane, hydrogels, collagens, hyalurons, proteins and other polymers known to those skilled in the art. Polymers such as silicone and polyurethane are generally known to have mechanical elasticity values of less than 100 MPa. Hydrogels and collagens can also be made with mechanical elasticity values less than 20 MPa and greater than 1.0 MPa. Silicone, polyurethane and some cryogels typically have ultimate tensile strength greater than 100 or 200 kilopascals (KPa). Materials of this type can typically withstand torsions greater than 0.01 N-m without failing.

Nucleus 60 is biocompatible, compressible, and free floating within the confines of an annulus of tension-bearing windings 70. In use of the prosthetic disc 20, a compressive force applied to the nucleus by opposing superior and inferior forces on the end caps 32 and 34 will result in elastic deformation of the nucleus 60 and its radially outward expansion against the surrounding winding 70 of the annulus. Thus, the axially applied compressive force on the nucleus is converted to an outward pressure on the several layers of the peripheral windings 70 as occurs in the natural human disc. In preferred embodiments, where the fiber strand pitch angle 71 alternates from layer to layer, the resulting arrangement of strands, while not actually woven, allows the several layers of tension-bearing material in the windings 70 to cooperate to withstand large outward forces generated by axial compression and radial expansion of the central nucleus 60.

A plurality of closely spaced fingers 72 may extend radially alongside one another from the periphery of the end plate 40, and similar fingers 74 may be arranged symmetrically oppositely on the end plate 42. Each of the fingers 72 and 74 may curve arcuately away from the opposite one of the end plates 40 and 42 and thus toward the adjacent end cap 32 or 34, in the form of a shallow hook to receive the flexible tension-bearing strands of the winding 70. The number of fingers 72 on the end plate 40 is preferably equal to the number of fingers 74 on the end plate 42, in order to have the winding 70 be of a regular and equally spaced arrangement about the periphery of each of the end plates 40 and 42. For example, there may be about 40 of such fingers 72 or 74 spaced apart around each end plate 40 or 42. The fingers 72 and 74 may have rounded edges and be smooth and polished to avoid wearing through the strands of the winding 70.

A peripheral rim 76 is provided on each of the end caps 32 and 34 and extends axially of the disc prosthesis 20 toward the adjacent end plate 40 or 42. The rim 76 thus surrounds at least the nearest part of the associated end plate 40 or 42, in contact with or at least closely outwardly adjacent the tip of each of the fingers 72 or 74. The rim 76 thus prevents the tension-bearing strands of the winding 70 from being disengaged from the fingers 72 or 74 when the winding 70 is relieved of tension and becomes slack, as when the prosthetic disc 22 is subjected to compression or when the end plates 40, 42 are inclined with respect to each other as a result of flexure of the spine in which the disc 20 may be implanted.

Figure 5:
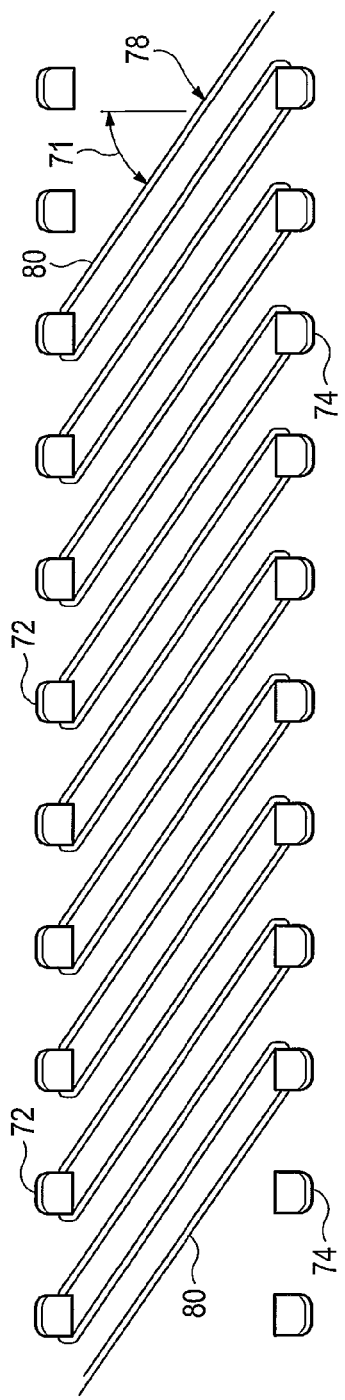
FIG. 5 is a schematic view of a first arrangement of winding a strand of a flexible tension-bearing material around the fingers spaced apart along the periphery of each end plate of the prosthetic disc.
Figure 6:
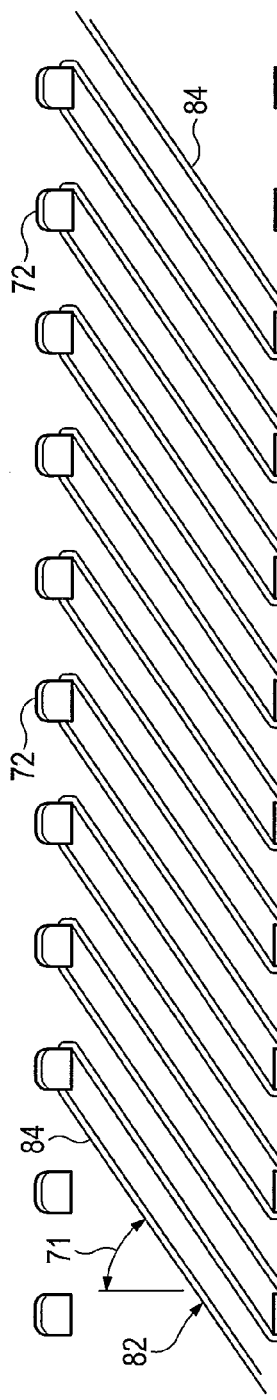
FIG. 6 is a schematic view of a second arrangement of winding a strand of a flexible tension-bearing material around the fingers spaced apart along the periphery of each end plate of the prosthetic disc.
Figure 7:
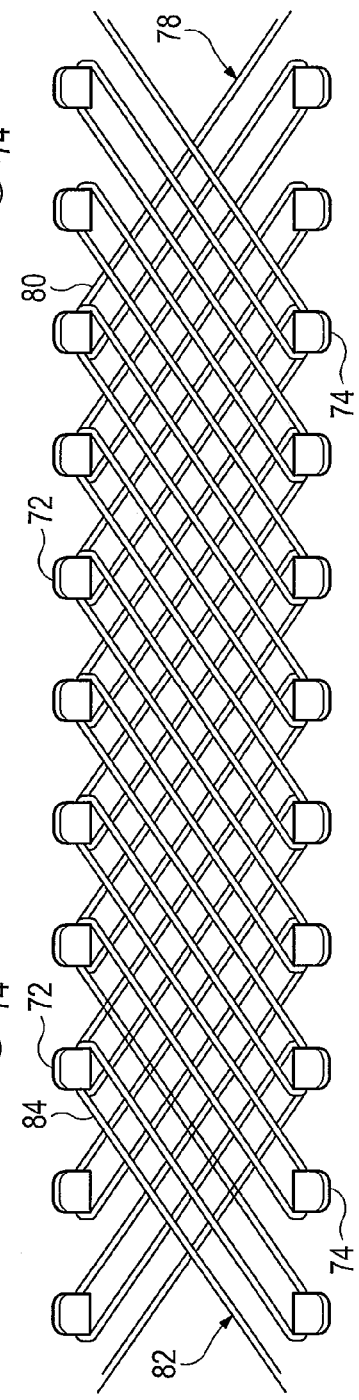
FIG. 7 is a schematic view showing the arrangement of two overlapping differently oriented layers of windings of tension-bearing material around the periphery of the prosthetic disc.

As may be seen in FIGS. 5, 6, and 7, in a simplified, schematic form, the winding 70 may comprise several layers, of which, for the sake of clarity, only two layers are shown in the drawings. In a layer 78, as shown in FIG. 5, a strand of tension-bearing material that may be in the form of a fine braided cord is wound about the entire periphery of the prosthetic disc 20 in a diagonal fashion so that each leg 80 of the layer 78 extends diagonally from upper left to lower right and then back from lower right to upper left as seen looking toward the prosthetic intervertebral disc 20. In a layer 82 of the winding 70, as shown in FIG. 6, each length between fingers, or leg 84 of the strand of tension-bearing fiber material extends from upper right to lower left and similarly back from lower left to upper right about the entire periphery of the prosthetic intervertebral disc 20. The legs 80 and 84 thus extend in their respective directions at a pitch angle 71, with respect to the central axis of the disc 20, in the range of about 15°-45° and preferably about 25°-35° and most preferably about 30°.

As shown in FIG. 7, the winding 70 may include equal numbers of layers 78 and 82 overlying one another and also wound around the fingers 72 and 74. The layers 78 and 82 may be wound alternatingly with each layer 78 followed by one layer 82 or with two or three layers 78 followed alternatingly by two or three layers 82 of opposite pitch, until the required total amount of tension-bearing material has been wound, depending on the composition and thickness of the tension-bearing strands used.

As an example, in a disc in which each of the end plates 40, 42 has 40 fingers 72, a winding 70 of 2 to 4 layers 78 and 2 to 4 layers 82 wound alternatingly would be adequate using a fine cord, such as a braided cord of ultra high molecular weight polyethylene fibers 0.1 to 1 millimeter in diameter, or of 4-0, 3-0, or 2-0 thread size, where the end plates 40 and 42 are separated by about 5-10 millimeters and the pitch angle 71 of each leg of the winding is about 30-45 degrees.

The amount of tension required in each leg 80 of tension-bearing material in the winding 70 will depend in part upon the composition of the nucleus 60, whose compressibility and elasticity will be a factor together with the tension and elasticity of the winding 70, in determining the amounts of forces needed to move the end plates 40 and 42 with respect to each other in rotation, compression, translation, or inclination (as in bending of the spine), relative to a neutral condition before implantation of the prosthetic disc 20.

Figure 12:
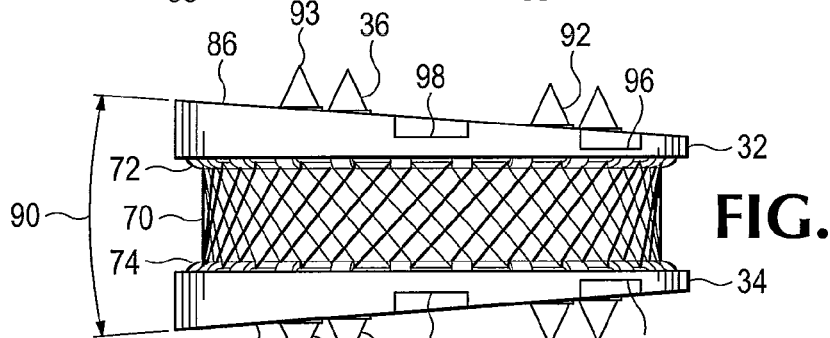
FIG. 12 is a sagittal elevational view taken from the left side of a disc prosthesis similar to that shown in FIG. 2, as indicated by the line 12-12 in FIG. 2, showing end caps whose superior and inferior end surfaces are oriented at an angle to each other to provide for a desired amount of lordosis in a spine in which the disc prosthesis is to be implanted.
Figure 13:
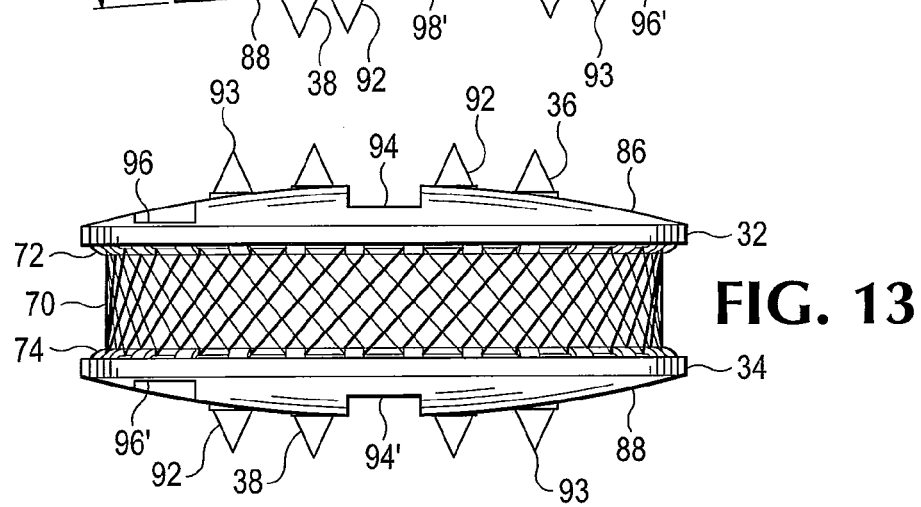
FIG. 13 is an elevational view taken from a dorsal side of a disc prosthesis shown in FIG. 2, showing end caps whose end surfaces are convex, to accommodate a common concave shape of the ends of superior and inferior vertebral bodies against which the disc prosthesis is to bear when implanted.

The outer end surfaces 86 and 88 of the end caps 32 and 34 of the prosthetic disc 20, the surfaces that will come into contact with the adjacent vertebral bodies 22 and 24, need to have an orientation relative to one another that ranges from parallel to an angle 90 of several degrees, as shown in FIG. 12, in order to accommodate to the proper relative positions of the adjacent superior and inferior vertebrae in the part of the spine in which the particular prosthesis 20 is to be implanted. The outer end surfaces 86 and 88 of the end caps 32 and 34 must thus have positions ranging from parallel to several degrees of inclination relative to each other to accommodate lordosis appropriately. Also, the outer end surfaces 86 and 88 of the end caps 32 and 34 may be convex, as shown in FIG. 13, in order to accommodate the concavity of some human vertebral end plates. These relative positions and shapes of the end surfaces 86 and 88 of the prosthetic disc 20 may be achieved by appropriately shaping one or both of the end caps 32 and 34. In the embodiment illustrated in FIGS. 1, 2, and 3, the outer end surfaces 86 and 88 of the prosthetic disc 20 abutting the adjacent vertebral bodies 22 and 24 are substantially parallel to one another.

Figure 10:
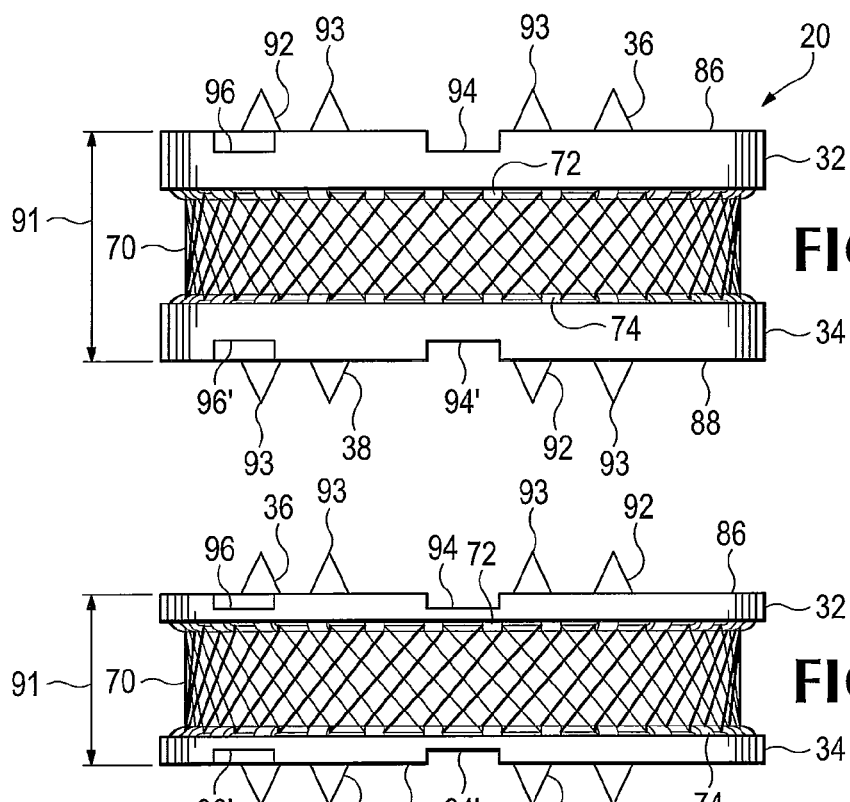
FIG. 10 is an elevational view taken from a dorsal side of the disc prosthesis shown in FIG. 2.
Figure 11:
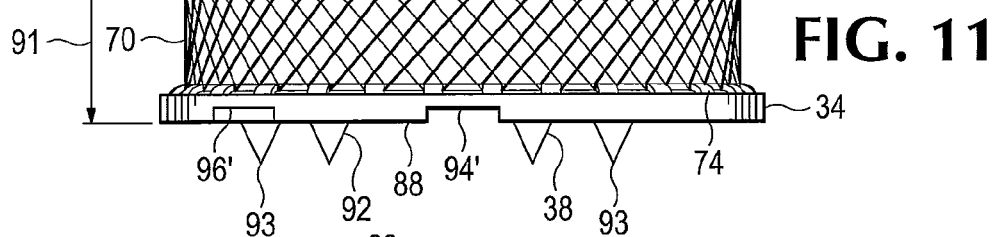
FIG. 11 is an elevational view taken from a dorsal side of a disc prosthesis similar to that shown in FIG. 2 but wherein the end caps are thinner than those shown in FIG. 10.

It is known that large variations exist among humans as to height, transverse and anterior/posterior size of the disc space, the concavity of the vertebral end plates, and the amount of lordosis in a spinal segment. Therefore, it is contemplated that prosthetic discs 20 will be manufactured in several different sizes, with interchangeable end caps 32 and 34 in a variety of thicknesses, inclinations, and amounts of convexity, so as to make the necessary selection available to the treating physician to insure a proper fit for a particular patient. Thus, with thinner end caps 32 and 34 shown in FIG. 11 the prosthetic disc 20 has a smaller height 91 than with the thicker end caps 32 and 34, as shown in FIG. 10. The prosthetic disc 20 can thus be customized in order to insure accurate anatomic seating of the prosthesis to a particular patient by selecting specific thicknesses, convexity, and angularity of the end caps 32 and 34 to be installed, immediately prior to implantation, from a set of end caps having a range of heights and inclinations.

The end caps 32, 34 in some embodiments may be slightly flexible, being of woven or braided metal fibers, wherein the fibers may be of materials selected from the group consisting of titanium, aluminum, vanadium, tantalum, cobalt/chrome alloy, stainless steel and nitinol. Alternatively, the end caps may comprise a polymeric or ceramic material in a form that provides a flexible pad having mechanical properties similar to those of a natural spinal disc end plate. In other embodiments the end caps may be rigid metal end plates, comprised of a biocompatible metal, such as for example, titanium/aluminum/vanadium alloy, tantalum, cobalt/chrome alloy, stainless steel or nitinol. End caps may be made from porous titanium in one embodiment.

Although in many embodiments sufficient adhesion can be obtained between the adjacent vertebral bodies 22 and 24 and the prosthetic disc 20 simply by the compressive and frictional forces provided on the prosthetic disc by the vertebral bodies, in preferred embodiments additional adhesion to the vertebral bodies may be obtained by incorporating surface modifications on the superior and inferior surfaces 86 and 88 of the prosthetic disc 20 that come into contact with the superior and inferior vertebral bodies 22, 24, respectively.

The modifications may include physical scoring or indentations of the surface, chemical irritants incorporated on the surface, biochemical agents modified on the surface, or small fibers that extend from the surfaces 86 and 88 to stimulate adhesion to a vertebral body or vertebral end plate. These fibers and surface modifications may induce an osteogenic reaction from the person to enhance attachment to the vertebral bodies.

Fixation may be induced in several ways, as by including open pores or rough surfaces, porous structures with undercuts, incorporation of osteoconductive or inductive agents, incorporation of other polymers such as polyester fabric or fibers, incorporation of other biologically active molecules such as bone morphogenic proteins, or collagen, or providing metal solid or mesh, rough surface with features greater than 5 nanometers. The roughness of the surface may include undercut pores which may be around 0.5 mm in diameter, or up to 2 mm in diameter, similar to a sponge. It is anticipated that there may be many ways of modifying the surface characteristics of the prosthetic disc 20 to achieve the same objective of providing cellular in-growth or attachment by collagen or bone.

One preferred embodiment for mediating adhesion may be understood by referring to FIG. 4, which depicts surface spikes 92 extending proud by a distance 89 in the range of about 2-4 mm and preferably approximately 2 mm on the superior and inferior end caps 32, 34, respectively. The spikes 92 may be formed as a part of the process of intraoperatively assembling the prosthetic disc 20, by utilizing specially configured screws 36 and 38, shown in enlarged detail view in FIGS. 4A, and 4B. The screws 36 and 38 are tightened with their threaded shafts 52 extending through the bores 50 of the end caps 32 and 34 into the threaded bores 54, to attach them to the end plates 40 and 42. Thereafter, continuing to twist the drive head 95 of each fastener until the fastener breaks off at its narrow waist 53, seen best in FIG. 4A, leaves a pointed end or small rough surface 93 to be embedded into the adjacent vertebral body. Such screws 36 and 38 may initially be, for example, about 12 mm in length 100, including the twist off drive head portion 95. The head 105 may be between 3 and 5 mm in diameter, to be countersunk into a recess 48 in an end cap 32 or 34, and the shaft 52 may be between about 1.5 and 3 mm in diameter. Machine threads are provided on the shaft 52 to mate with the threaded bore 54 of the end plate 40 or 42 to attach the end cap 32 or 34 to the main part of the prosthesis. The middle portion or waist 53, of the body of the screw 36 or 38 narrows in what may be conical shape, or preferably a pyramidal shape, so that when a certain amount of torque is applied after the screw is tightened into the end plate 40 or 42 the screw will break off in the narrowest portion of the waist 53 leaving a pyramidal shaped spike 92, about 2 to about 3 mm on each side 106 and about 2 to about 3 mm in its height 89, and with the previously mentioned point 93. The screws 36 and 38 may be made of the same material as the modular end cap 32 or 34, such as a titanium alloy or a cobalt/chrome alloy, or of another suitable biocompatible metal not likely to react electrolytically with the end caps or end plates.

In some embodiments, the surfaces 86 and 88 of end caps 32 and 34 that come in contact with the superior and inferior vertebral bodies 22 and 24 may comprise porous titanium. The bone-contacting surfaces 86 and 88 of the end caps 32 and 34 may also further comprise hydroxyapatite, bone morphogenic proteins, or polycrystalline alumina ($Al_2O_3$) coatings.

Figure 8:
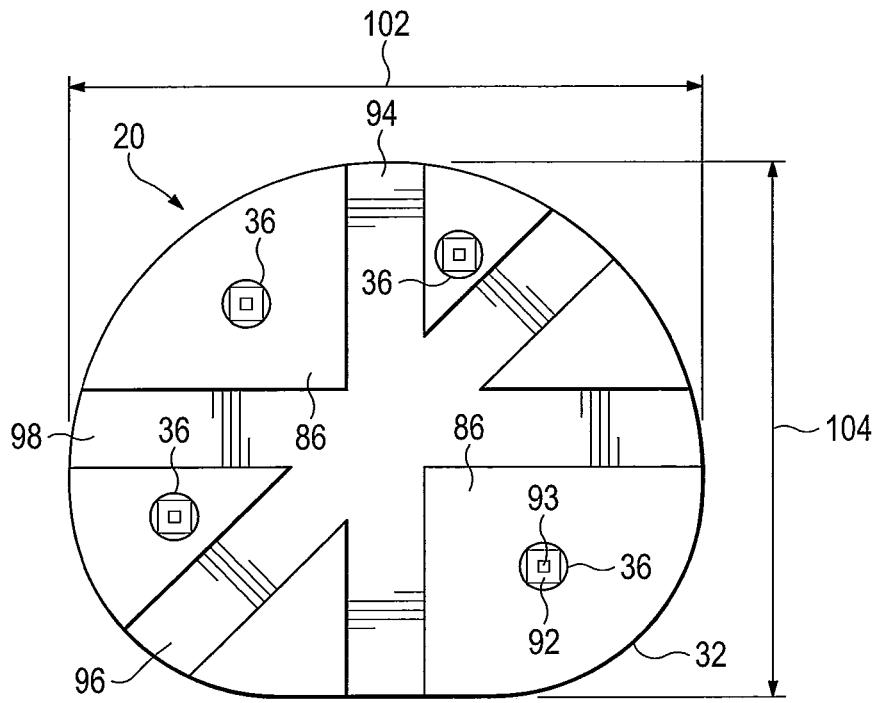
FIG. 8 is a top plan view of a first, or superior, end cap of the disc prosthesis shown in FIG. 2.
Figure 9:
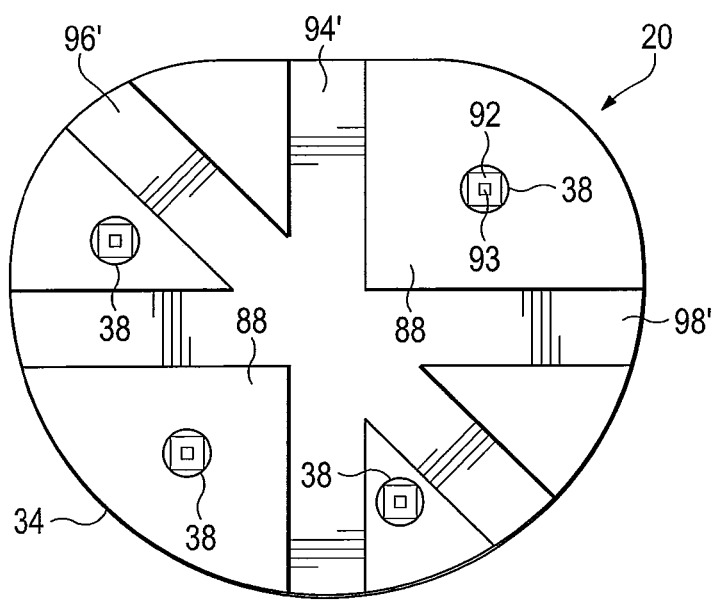
FIG. 9 is a bottom plan view of the second, or inferior, end cap of the disc prosthesis shown in FIG. 2.

In some embodiments, as seen best in FIGS. 8 and 9, the end caps 32 and 34 each define a plurality of angulated mounting grooves in their exterior surfaces 86 and 88, wherein each groove in the superior end of the disc prosthesis 20 has a corresponding parallel groove on the inferior end of the disc prosthesis. These angulated mounting grooves serve as guides for accurate placement of the prosthetic disc 20 between the vertebral bodies 22 and 24 using an insertion tool 26, as the mounting grooves are engaged by the arms 28 and 30 of the insertion tool 26 to allow the prosthesis 20 to slide linearly into the space formerly occupied by a diseased disc while a distraction tool, which may include or serve as an insertion tool 26, holds open the disc space between the vertebral bodies 22 and 24. Distraction tools may be of various types such as spreading and insertion forceps well known to those in the art, and the tool shown as the insertion tool 26 in FIG. 1 is intended to be representative only in a general and not a specific sense. It will be appreciated that numerous designs of distraction tools and insertion tools are contemplated. An insertion tool must be able to engage the prosthetic disc 20 via one or more of the mounting grooves, as described more fully below.

In particular, embodiments are contemplated that provide for an anterior to posterior mounting groove 94, and at least one other groove 96 or 98 oriented at an angle of 45 or 90 degrees to the anterior to posterior groove 94. In one embodiment of the prosthetic disc 20 all three mounting grooves are provided on each end cap 32 and 34, thereby providing a first, or anterior to posterior groove 94, a first diagonal or anterolateral groove 96, oriented 45 degrees to the first groove 94, and a lateral groove 98 oriented 90 degrees to the first groove 94 on the upper end cap 32. (FIGS. 2 and 8). Similarly, the lower end cap 34 has three grooves located symmetrically and parallel with corresponding grooves 94, 96, and 98 on the upper end cap 32, thereby providing an anterior to posterior groove 94', a diagonal groove 96' oriented 45 degrees to groove 94', and a lateral groove 98' oriented 90 degrees to groove 94' as may be seen in FIG. 9. Thus, using groove pair 96 and 96' allows insertion of the prosthetic disc 20 from an anterolateral approach to the lumbar spine. This approach would be highly advantageous when inserting the device into L4-5 disc space. The L4-5 disc space is bordered anteriorly by the bifurcation of the iliac veins and arteries which make it difficult to obtain direct anterior access to that intervertebral disc space. Additionally, using the groove-pair 98 and 98' allows insertion of the device into the L2-3, L3-4, and possibly the L4-5 intervertebral disc levels, from a direct lateral retroperitoneal flank approach to the spine.

The prosthetic intervertebral disc 20 may optionally further comprise a peripheral elastomeric biocompatible sheet, for example of silicone, thereby encapsulating the entire annulus winding 70 and providing a single convenient covering to prevent extrusion of any particulate debris from the annular or nucleus fibers of the prosthetic device 20 for replacing a damaged intervertebral disc in a human. The elastomeric sheet covering, if used, will be used to seal off the annulus and the nucleus from the surrounding tissues, thus eliminating particulate debris release.

Typical molding, casting and computer-aided machining (CAM) techniques can be used to form the end caps 32 and 34 and end plates 40 and 42. Prosthetic discs 20 may be made to have a geometry consistent with that of a natural disc. Although the disc size can, of course, be varied, a suitable size for the prosthetic disc 20 is to have an area in plan view, as seen in FIG. 8, of about 1100 mm², a major diameter 102 of about 44 mm and a minor diameter 104 of about 30 mm.

In use, the disc prosthesis 20 is implanted using surgical techniques known to those in the art. In one illustrative embodiment where the prosthesis will be placed in the lumbosacral region, the preparation for the retroperitoneal surgery may be the same as in abdominal surgery. A retroperitoneal or transperitoneal anterior, anterolateral or extreme lateral approach is used to expose the disc spaces. The great vessels and ureters are identified and protected. The anterior longitudinal ligament is incised transversely and opened like a door to expose the injured or degenerated disc. The diseased natural disc and cartilaginous end plates are removed with a curette, periosteal elevator, chisel, rongueurs, or power drill, for example. Using a distraction tool to apply controlled distraction to the disc space, the remaining disc is visualized and removed, thereby performing a complete discectomy. Using fluoroscopy it is verified that the optimal angle between the bony end plates has been achieved to restore the desired lordosis. With the spacing and degree of lordosis optimized, the prosthesis of the appropriate size is then selected and loaded onto the guiding arms 28 and 30 of the insertion tool 26. Depending on the position of the distraction tool in the patient, the appropriate pair of mounting grooves on the prosthetic disc 20 is engaged with the insertion tool in order to insure the prosthesis slides into the interverbral space in the correct orientation.

As noted above, the plurality of mounting grooves 94, 96, and 98 afford multiple approaches for the insertion tool 26 that will allow proper placement of the prosthesis. Thus in certain embodiments, prosthetic disc 20 of the invention may be placed between vertebrae 22 and 24 using (i) an anterior approach by engaging slot-pair 94 and 94' with an insertion tool 26, (ii) an anterolateral approach by engaging slot-pair 96 and 96' with the insertion tool 26, and (iii) a lateral approach by engaging slot-pair 98 and 98' with the insertion tool 26 (FIG. 1). It will be further understood that by using an appropriate insertion tool oriented 180 degrees to the above anterolateral approach the prosthesis may be placed using (iv) a posterolateral approach by engaging slot-pair 96 and 96'.

In preferred embodiments, the center of the placed prosthesis will correspond to the sagittal and coronal midline, and this placement may be verified using lateral and anterior to posterior fluoroscopy. After the proper placement of the prosthesis is confirmed, the spikes 92 on the superior and inferior end faces 88, 90 of the prosthesis 20 are impacted into the superior and inferior vertebral bodies, respectively. The distraction tool is then released and removed from the prosthesis and disc space. The anterior longitudinal ligament and a portion of the annular ligament, if preserved, are then closed with sutures. The overlying fascia, soft tissue, and skin are closed. The patient is then mobilized.

While several embodiments of the present invention have been described, it is obvious that many changes and modifications may be made without departing from the spirit and scope of the invention.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A prosthetic intervertebral disc comprising:
   (a) a resiliently flexible and compressible nucleus having an upper face, a lower face, and a peripheral outer surface extending between said upper and lower faces;
   (b) an upper end plate located proximate said upper face and having a first plurality of fingers extending radially outward and extending curvingly away from the upper face of the nucleus in the form of shallow hooks having respective tips extending axially away from the upper face of the nucleus;
   (c) a lower end plate located proximate said lower face and having a second plurality of fingers extending radially outward and extending curvingly away from the lower face of the nucleus in the form of shallow hooks having respective tips extending axially away from the lower face of the nucleus;
   (d) a strand of flexible tension-bearing material separate from the nucleus extending around one of the first plurality of fingers and to and around a respective one of the second plurality of fingers, separate from but adjacent said peripheral outer surface of said nucleus, as a winding interconnecting said upper and lower end plates with each other; and
   (e) a respective end cap located axially adjacent and covering each of said end plates, each said end cap including a peripheral rim, the peripheral rim extending from the end cap and in an axial direction with respect to the prosthetic intervertebral disc, toward the adjacent end plate, and being located radially outwardly adjacent to and closely surrounding said tips of said plurality of fingers of the respective end plate to which it is attached.

2. A prosthetic intervertebral disc comprising:
   (a) a resiliently flexible and compressible nucleus having an upper face, a lower face, and a peripheral outer surface extending between said upper and lower faces;
   (b) an upper endplate located proximate said upper face and having a first plurality of fingers extending radially outward and having respective tips;
   (c) a lower end plate located proximate said lower face and having a second plurality of fingers extending radially outward and having respective tips;
   (d) a strand of flexible tension-bearing material separate from the nucleus, extending around one of the first plurality of fingers and to and around a respective one of the second plurality of fingers, separate from but adjacent said peripheral outer surface of said nucleus, as a winding interconnecting said upper and lower end plates with each other; and
   (e) a respective end cap located axially adjacent and covering each of said end plates, each said end cap including a peripheral rim, the peripheral rim extending from the end cap and in an axial direction with respect to the prosthetic intervertebral disc and being located radially outwardly adjacent to and closely surrounding said tips of said fingers of the respective end plate to which it is attached; and
   (f) wherein said tips of said fingers of at least one of said first and second pluralities of fingers curve arcuately toward an adjacent said respective end cap, the fingers thereby defining hooks having tips directed toward the adjacent respective end cap and around which said strand of flexible tension-bearing material extends.

3. The prosthetic intervertebral disc of claim 1 wherein said nucleus includes an outer membrane surrounding and containing a quantity of a gel material.

4. The prosthetic intervertebral disc of claim 3 wherein said gel material is an elastomeric material.

5. The prosthetic intervertebral disc of claim 3 wherein said gel material is a hydrogel.

6. The prosthetic intervertebral disc of claim 1 wherein said nucleus includes an outer membrane surrounding and containing a quantity of water.

7. The prosthetic intervertebral disc of claim 1 wherein one of said end caps has a respective thickness selected to establish a predetermined height of said prosthetic intervertebral disc.

8. A prosthetic intervertebral disc comprising:
   (a) a resiliently flexible and compressible nucleus having an upper face, a lower face, and a peripheral outer surface extending between said upper and lower faces;
   (b) an upper end plate located proximate said upper face and having a first plurality of fingers extending radially outward and having respective tips;
   (c) a lower end plate located proximate said lower face and having a second plurality of fingers extending radially outward and having respective tips;
   (d) a strand of flexible tension-bearing material separate from the nucleus extending around one of the first plurality of fingers and to and around a respective one of the second plurality of fingers, separate from but adjacent said peripheral outer surface of said nucleus, as a winding interconnecting said upper and lower end plates with each other; and
   (e) a respective end cap located axially adjacent and covering each of said end plates, each said end cap including a peripheral rim, the peripheral rim extending from the end cap and in an axial direction with respect to the prosthetic intervertebral disc and being located radially outwardly adjacent to and closely surrounding said tips of said fingers of the respective end plate to which it is attached, and wherein one said respective end cap has a generally convex outer end surface facing axially away from the adjacent end plate.

9. The prosthetic intervertebral disc of claim 1 wherein said strand of flexible tension-bearing material is arranged in said winding as a plurality of legs each extending at a respective first pitch angle in a helical orientation between respective ones of the pluralities of fingers.

10. The prosthetic intervertebral disc of claim 9 including a second strand of flexible tension-bearing material arranged in said winding as a plurality of legs each extending at a respective second pitch angle in a helical orientation between respective ones of the pluralities of fingers.

11. A prosthetic intervertebral disc comprising:
   (a) a resiliently flexible and compressible nucleus having an upper face, a lower face, and a peripheral outer surface extending between said upper and lower faces;
   (b) an upper end plate located proximate said upper face and having a first plurality of fingers extending radially outward and having respective tips;
   (c) a lower end plate located proximate said lower face and having a second plurals of fingers extending radially outward and having resective tips;
   (d) a strand of flexible tension-bearing material separate from the nucleus extending around one of the first plurality of fingers and to and around a respective one of the second plurality of fingers, separate from but adjacent said peripheral outer surface of said nucleus, as a winding interconnecting said upper and lower end plates with each other; and
   (e) a respective end cap located axially adjacent and covering each of said end plates, each said end cap including a peripheral rim, the peripheral rim extending from the end cap and in an axial direction with respect to the prosthetic intervertebral disc and being located radially outwardly adjacent to and closely surrounding said tips of said fingers of the respective end plate to which it is attached, wherein said tips of said fingers curve arcuately and extend in an axial direction relative to the prosthetic intervertebral disc toward the respective adjacent said end cap, and wherein a part of said respective adjacent said end cap adjacent said peripheral rim thereof is located in contact with said tips of said fingers.

12. A prosthetic intervertebral disc comprising:
   (a) a resiliently flexible nucleus having an upper face, a lower face, and a peripheral outer surface extending between said upper and lower faces;
   (b) an upper end plate located proximate said upper face and having a first plurality of fingers extending radially outward from said upper face of said nucleus, being curved arcuately upward, and having respective tips extending upwardly away from said nucleus in the form of hooks;
   (c) a lower end plate located proximate said lower face and having a second plurality of fingers extending radially outward from said lower face of said nucleus, being curved arcuately downward, and having respective tips extending downwardly away from said nucleus in the form of hooks;
   (d) a strand of flexible tension-bearing material separate from the nucleus extending as a winding around said tips of respective ones of the first plurality of fingers and extending to and around said tips of respective ones of the second plurality of fingers, separate from but adjacent said peripheral outer surface of said nucleus and interconnecting said upper and lower end plates with each other, the respective tips of the respective fingers of said first and second pluralities serving as hooks around which said strand of flexible tension-bearing material extends; and
   (e) a respective end cap attached mechanically to and covering each of said end plates, each said end cap including a peripheral rim, the peripheral rim extending from the respective end cap in an axial direction with respect to the prosthetic intervertebral disc, toward the nucleus, and being located outwardly adjacent to and surrounding said tips of said plurality of fingers of the respective end plate to which the respective end cap is attached.

13. The prosthetic intervertebral disc of claim 12 wherein said nucleus includes an outer membrane surrounding and containing a quantity of a gel material.

14. The prosthetic intervertebral disc of claim 12 wherein said nucleus includes an outer membrane surrounding and containing a quantity of water.

15. The prosthetic intervertebral disc of claim 12 wherein one of said end caps has a respective thickness selected to establish a predetermined height of said prosthetic intervertebral disc.

16. The prosthetic intervertebral disc of claim 12 wherein one of said end caps has an outer face having a generally convex surface shape.

17. The prosthetic intervertebral disc of claim 12 wherein said strand of flexible tension-bearing material is arranged in said winding as a plurality of legs each extending at a respective first pitch angle between respective ones of the pluralities of fingers.

18. The prosthetic intervertebral disc of claim 17 including a second strand of flexible tension-bearing material arranged in said winding as a plurality of legs each extending at a respective second pitch angle between respective ones of the pluralities of fingers.

19. A prosthetic intervertebral disc comprising:
   (a) a resiliently flexible and compressible nucleus having an upper face, a lower face, and a peripheral outer surface extending between said upper and lower faces;

(b) an upper end plate located proximate said upper face and having a first plurality of fingers extending radially outward and having respective tips;
(c) a lower end plate located proximate said lower face and having a second plurality of fingers extending radially outward and having respective tips;
(d) a strand of flexible tension-bearing material separate from the nucleus extending around one of the first plurality of fingers and to and around a respective one of the second plurality of fingers, separate from but adjacent said peripheral outer surface of said nucleus, as a winding interconnecting said upper and lower end plates with each other; and
(e) a respective end cap located axially adjacent and covering each of said end plates, each said end cap including a peripheral rim, the peripheral rim extending from the end cap and in an axial direction with respect to the prosthetic intervertebral disc and being located radially outwardly adjacent to and closely surrounding said tips of said fingers of the respective end plate to which it is attached, wherein said tips of said fingers curve arcuately toward the adjacent said respective end cap, and wherein said peripheral rim of said adjacent said respective end cap is located in contact with said tips of said fingers.

* * * * *